(12) United States Patent
Yoshikawa

(10) Patent No.: US 8,784,921 B2
(45) Date of Patent: Jul. 22, 2014

(54) METHOD FOR CONCENTRATING LIPIDS

(75) Inventor: Kazuhiro Yoshikawa, Hachioji (JP)

(73) Assignee: Nippon Suisan Kaisha, Ltd., Tokyo (JP)

( * ) Notice: Subject to any disclaimer, the term of this patent is extended or adjusted under 35 U.S.C. 154(b) by 215 days.

(21) Appl. No.: 13/120,875

(22) PCT Filed: Sep. 24, 2009

(86) PCT No.: PCT/JP2009/066529
§ 371 (c)(1),
(2), (4) Date: Apr. 25, 2011

(87) PCT Pub. No.: WO2010/035749
PCT Pub. Date: Apr. 1, 2010

(65) Prior Publication Data
US 2011/0189374 A1 Aug. 4, 2011

(30) Foreign Application Priority Data

Sep. 26, 2008 (JP) .................. P2008-248986

(51) Int. Cl.
A22C 29/02 (2006.01)
(52) U.S. Cl.
USPC .......................................... 426/417; 426/643
(58) Field of Classification Search
USPC ................................................ 426/417, 643
See application file for complete search history.

(56) References Cited

U.S. PATENT DOCUMENTS

| | | | |
|---|---|---|---|
| 6,399,105 B1 | 6/2002 | Collin | |
| 6,800,299 B1 * | 10/2004 | Beaudoin et al. | 424/522 |
| 2003/0054084 A1 | 3/2003 | Hruschka et al. | |
| 2009/0061067 A1 * | 3/2009 | Tilseth et al. | 426/602 |
| 2010/0143571 A1 * | 6/2010 | Breivik | 426/643 |
| 2010/0226977 A1 * | 9/2010 | Tilseth | 424/456 |
| 2011/0189374 A1 * | 8/2011 | Yoshikawa | 426/601 |

FOREIGN PATENT DOCUMENTS

| | | |
|---|---|---|
| DK | WO2007080515 A1 * | 7/2007 |
| EP | 0 848 911 | 6/1998 |
| EP | 2 006 296 | 12/2008 |
| JP | 52-76455 | 6/1977 |
| JP | 52-114046 | 9/1977 |
| JP | 54-76858 | 6/1979 |
| JP | 2-215351 | 8/1990 |
| JP | 8-325192 | 12/1996 |
| JP | 10-179038 | 7/1998 |
| JP | 2909508 | 4/1999 |
| JP | 2003-003190 | 1/2003 |
| JP | 2004-026767 | 1/2004 |
| SU | 220741 | 10/1970 |
| WO | 00/23546 | 4/2000 |
| WO | 2007/080514 | 7/2007 |
| WO | 2007-105734 | 9/2007 |
| WO | 2008/117062 | 10/2008 |
| WO | 2009/027692 | 4/2009 |

OTHER PUBLICATIONS

Edible oils and processing—"Saishin Shokuhin Kakou Koza—Shokuyo Yushi to Sono Kako" edited by Tetsujiro Ohara, published by Kenpakusha, 1981, pp. 49-74—machine translation.
Fish oil and sardine—"Gyoyu to Maiwasi" edited by Hichiro Matsushita, published by Koseisha Koseikaku, 1991, pp. 21-28—machine translation.
"Bailey's Industrial Oil and Fat Products" edited by Y. H. Hui, published by John Wiley & Sons, 1996, Fifth Edition, vol. 1, pp. 336-347.
Clarke, "The Biochemical Composition of Krill, *Euphausia superba* Dana, From South Georgia", J. exp. mar. Biol. Ecol., 1980, vol. 43, pp. 221-236.
Fedotova, et al., "Changes in the fatty acid composition of lipids in Okean krill paste during cooking", Vopr Pitan, No. 1, pp. 70-73, 1977, with English translation.
Sikorski, et al., "The Utilization of Krill for Food", Food Process Eng., vol. 1, 1980, pp. 845-855.
Osnes,et al., "Peptide Hydrolases of Antarctic Krill, *Euphausia superba*", Comp. Biochem. Physiol., vol. 82B, No. 4, pp. 599-606, 1985.
Sikorski, et al., "The Utilization of Krill for Food", Food Process Engineering, vol. 1, pp. 845-855, 1980.

* cited by examiner

*Primary Examiner* — Carolyn Paden
(74) *Attorney, Agent, or Firm* — Hamre, Schumann, Mueller & Larson, P.C.

(57) ABSTRACT

As a method for an efficient concentration of lipid components from food materials, a method for concentrating lipids contained in a crustacean, which comprises heating squeezed liquid prepared by squeezing the whole crustacean or a part thereof and separating the heated squeezed liquid into solids containing lipid components and liquid containing water-soluble components. Those are useful as the method by which lipids abundantly containing the phospholipid are prepared easily and at a low cost. Furthermore, the solids containing the lipids prepared by said method or a dried product thereof, lipids extracted therefrom and a composition abundantly containing the useful lipids derived from crustaceans are useful as materials for pharmaceuticals, ingredients for foods or feed, etc.

10 Claims, No Drawings

METHOD FOR CONCENTRATING LIPIDS

TECHNICAL FIELD

The present invention relates to a method for producing lipids or, particularly, phospholipid contained in the crustacean in efficiently or relates to a composition wherein lipids which are able to be used as ingredients for food, feed, etc. are concentrated.

BACKGROUND ART

Edible lipids have been manufactured industrially from old times. For example, in the case of soybean oil which is most abundantly manufactured at present, after washing soybean seeds, outer skins thereof are removed if necessary and then the soybean seeds are crushed/made flat by compression and extracted with an organic solvent using, in many cases, hexane of about 50 to 60° C. After that, the extract is filtered and the solvent is removed therefrom (by means of distillation in many cases) to give crude oil. The crude oil is further filtered or centrifuged to remove the insoluble fractions and water is added thereto to remove water-soluble substances (degumming) followed by carrying out the steps of deacidification, decolorization and deodorization to give a product. Usually, manufacture of lipids from a raw material containing high amount of lipids such as plant seeds is relatively easy (Non-Patent Document 1). On the other hand, in the case of animal raw materials, oil is usually separated out only by and heating of the raw material after washing. Therefore, the product is able to be more easily manufactured. In the case of fish for example, since a liquid part is spontaneously separated into an aqueous part and a crude oil when the raw material is boiled and squeezed, fish oil is able to be manufactured by purifying the oil (Non-Patent Document 2). However, the lipids prepared by the methods are mainly triglycerides.

It has been known that phospholipid, a class of the lipids, has health functions such as an improvement in fatty liver caused by choline deficiency, a reduction in LDL (bad cholesterol) in blood and an increase in HDL (good cholesterol) in blood. Additionally, improvement in neuropathy caused by hypertension and acetylcholine deficiency, promotion of absorption of oil-soluble vitamins, etc. is expected. Phospholipid has been mostly separated and purified from soybean seed or egg yolk. In the case from soybean seed, phospholipid is contained in a fraction which is removed as an insoluble matter during a degumming step in the manufacturing steps of soybean oil and it is decolorized and dried to obtain a phospholipid product called lecithin (Non-Patent Document 3). Soybean oil has a very big market and phospholipid as a by-product thereof is also produced in large quantities. In the case of egg yolk, since about one-third of its weight is lipids and about one-third of lipids are phospholipids, extraction and purification of phospholipid are relatively easy. However, in view of efficient extraction of phospholipid and maintenance of its stability, it is necessary that water is previously removed from the raw material egg yolk. Dried egg yolk is manufactured by inputting of heat cost and phospholipid is extracted therefrom.

With regard to other raw materials containing a relatively high amount of phospholipid, marine products such as marine fish egg and krill have been known. However, when those raw materials are compared with egg yolk, content of phospholipid in the raw material is low and other impurities such as organic acids are abundant. Therefore, purification is not easy. With regard to preparation of lipids from marine products, there have been various proposals up to now such as a method where the material is previously dried and then lipids are extracted therefrom, e.g., a raw material marine product is dried so as to make the water content 10% or less by weight and then lipids are extracted therefrom (Patent Document 1), a method where a raw material is dried by means of freeze-drying and then lipids are extracted therefrom (Patent Document 2), a method where an organic solvent is used, e.g., lipids are extracted from the raw material fish/shellfish with a mixed solution of acetone and water, (Patent Document 3) and a method where, in extraction of lipids from the starting krill, acetone is used as the first stage (Patent Document 4). However, any of those methods has problems such as difficulty in terms of cost, complicatedness in the steps and limitation in the use due to legal restrictions.

Highly unsaturated fatty acids have been known to have a preventing/improving activities for lifestyle-related diseases (such as arteriosclerosis, hyperlipemia and dementia) and an immunosuppressive activity (such as reduction in allergy and atopy). Furthermore, EPA is expected for its effect of prevention of circulatory diseases such as reduction in neutral fats and suppression of platelet aggregation while DHA is expected for its effect of growth and maintenance of function of nerve tissues and improvement in eyesight (Non-Patent Document 4). Lipids from marine products are promising not only as a supplying source for phospholipid but also as a supplying source for highly unsaturated fatty acids such as EPA and DHA. However, as mentioned above, marine products contain many impurities such as organic acids including amino acids and fatty acids. Therefore, extraction and purification of lipids therefrom have not been easy.

A method in which proteins are obtained by coagulating protein components in krill, which is a type of crustacean, by heating has been known in the past as a method for extracting proteins from krill (patent document 5). However, a coagulated product known as "Okean" obtained by this method was used in order to obtain proteins (non-patent document 5).

In addition, after the present application was filed, a method for obtaining a coagulated product by heating krill to 60 to 70° C. by means of hot water and then reheating the thus obtained aqueous solution of the supernatant liquid to 90° C. or higher was disclosed within the priority claim period (patent document 6).

Patent Document 1: JP08-325,192 A

Patent Document 2: JP2,909,508 B

Patent Document 3: JP2004-26767 A

Patent Document 4: WO 00/23546

Patent Document 5: SU227041

Patent Document 6: WO 09/027692

Non-Patent Document 1: "Saishin Shokuhin Kakou Kozo-Shokuyo Yushi to Sono Kako" edited by Tetsujiro Ohara, published by Kenpakusha, 1981, pages 49 to 74

Non-Patent Document 2: "Gyoyu to Maiwasi" edited by Hichiro Matsushita, published by Koseisha Koseikaku, 1991, pages 21 to 28

Non-Patent Document 3: "Bailey's Industrial Oil and Fat Products" edited by Y. H. Hui, published by John Wiley & Sons, 1996, Fifth Edition, Volume 1, page 336

Non-Patent Document 4: A. Clarke, *Journal of Experimental Marine Biology and Ecology*, 1980, Volume 43, No. 3, pages 221 to 236

Non-Patent Document 5: Vopr Pitan, No. 1, page 70 to 73, 1977

DISCLOSURE OF THE INVENTION

Problems to be Solved by the Invention

Objects of the present invention are to provide a method for efficient extraction of lipid components from crustaceans and to provide a method for effective utilization of the composition prepared thereby.

Means for Solving the Problems

Under such a current status as described above, the inventors of the present invention have carried out intensive investigations repeatedly for a method of easy separation and concentration of lipids derived from crustaceans. As a result, they have found that lipids are localized in a solid part when a liquid part of crustaceans such as internal organs other than shells and muscles and internal tissues of the cephalothorax is previously separated and recovered by squeezing and the liquid part containing water-soluble impurities is heated to thermally coagulate proteins therein. Furthermore, they found that the impurities such as water-soluble organic acids, amino acids and peptides are able to be removed from the solid part by a simple means such as filtration and centrifugal separation. As a result, the present invention has been achieved. Accordingly, features of the present invention are as follows:

[1] A method for concentrating lipids contained in a crustacean, which comprises heating squeezed liquid prepared by squeezing the whole crustacean or a part thereof and separating the heated squeezed liquid into solids containing lipid components and liquid containing water-soluble components;
[2] The method for concentrating the lipids according to [1], wherein the whole crustacean or a part thereof is squeezed in an unheated state;
[3] The method for concentrating the lipids according to [1] or [2], wherein the squeezed liquid is heated at the temperature where proteins contained in the squeezed liquid is coagulated;
[4] The method for concentrating the lipids according to any one of [1] to [3], wherein the solid-liquid separation is carried out by means of filtration or centrifugal separation;
[5] The method for concentrating the lipids according to any one of [1] to [4], wherein the crustacean is a crustacean which belongs to the order of Euphausiaceae;
[6] Solids containing the lipid components prepared by the method described in any one of [1] to [5] or a dried product thereof;
[7] The solids containing the lipid components or a dried product thereof according to [6], wherein the lipid components' content is 30% or more by dry weight;
[8] The solids containing the lipid components or a dried product thereof according to [6] or [7], wherein 50% or more by weight of the lipid components is phospholipids;
[9] A method for producing lipids, which comprises preparing the lipids from the solids containing the lipid components or a dried product thereof prepared by the method described in any one of [1] to [5];
[10] The method for producing the lipids according to [9], wherein the method for preparing the lipids is carried out by any one of an extraction with an organic solvent, an extraction with an organic solvent after carrying out an enzymatic treatment and a supercritical extraction;
[11] A method for producing phospholipid, which comprises carrying out a supercritical extraction of the solids containing the lipid components prepared by the method described in any one of [1] to [5] or a dried product thereof to separate a triglyceride and preparing phospholipid from the residue after the extraction;
[12] A composition containing oils and fats, which contains lipids and proteins derived from the squeezed liquid of crustaceans and the content of the lipids is 35% or more by weight (dry weight); and
[13] A food or feed in which the composition containing oils and fats described in [12] is added as a supplying source for oils and fats.
[14] Solids obtained by washing solids containing lipid components obtained by the method described in any one of [1] to [5], or a dried product thereof, with water, or a dried product thereof.
[15] The solids containing lipid components or a dried product thereof described in [14], wherein the lipid component content is 40% or more.
[16] The solids containing lipid components or a dried product thereof described in [14] or [15], wherein 50% or more of the lipid components are phospholipids.

Effect of the Invention

In accordance with the present invention, it is possible that lipids which contain phospholipid abundantly is able to be manufactured easily and at low cost from crustaceans. It is also possible that solids containing the lipids prepared by said method or a dried product thereof wherein said solid is mainly composed of proteins and lipids derived from crustaceans is utilized as an ingredient for food and feed.

BEST MODE FOR CARRYING OUT THE INVENTION

The present invention relates to a method for concentrating lipids contained in crustaceans, which comprises heating a squeezed liquid prepared by squeezing the whole crustacean or a part thereof is heated and carrying out a solid-liquid separation into a solid which comprises lipid components and liquid which comprises water-soluble components. Although there is no particular limitation for the crustaceans which are a raw material of the present invention as long as it belongs to the class Malacostraca (a class to which shrimp, etc. belong), that which belongs to the order of Euphausiaceae or Decapodoceae is particularly used. Specifically, krill, shrimp, crab, etc. can be used and a part thereof such as cephalothorax of shrimps, shrimp shell meal and krill meal may be used as well. In that case, although there is no particular limitation for the type of the krill, *Euphausia pacifica* is particularly favorably used. Although the raw material may be heated and unheated as long as it is in a state which contains the lipids, it is preferable to use an unheated raw material such as fresh fish (raw one), frozen one or a raw material where the frozen one is thawed.

With regard to a method for squeezing, there is no particular limitation as long as it is a commonly used one. For example, an oil hydraulic squeezing machine, a screw press, a meat separator, a press dehydrating machine, a centrifugal separator or a combination thereof can be used. When collection of the lipids is an object, it is preferable that the whole crustacean or a part thereof is squeezed to obtain a squeezed liquid corresponding to an amount of 5 to 50% of the wet weight. When the squeezing is 5% or less, the lipids are not sufficiently compressed and extracted. When it is 50% or more, although the lipids are sufficiently squeezed, other impurities such as water-soluble organic acids, amino acids, peptides and proteins are contaminated and the steps for separation and extraction of the lipids thereafter become troublesome. However, when preparation of a solid containing the lipid component is an object, there is no problem even when the squeezing is conducted to an extent of 50% or more. Additionally, the shells after the squeezing produced in the preparation of squeezed liquid may be utilized as an ingredient of a feed, etc. according to a common utilizing method for krill.

After that, the resulting squeezed liquid is heated. There is no particular limitation for the heating method and any of commonly used methods can be used. Temperature for the heating may be temperature at which proteins are coagulated. For example, it is 50° C. or more and, it is preferably from 70 to 150° C. and particularly preferably from 85 to 110° C. Heating may be carried out under pressure or in vacuo. As a result, separation into a solid which comprises the lipid components and liquid which comprises water-soluble components is carried out. When a solid-liquid separation is carried out by means of, for example, filtration or centrifugal separation, solids containing the lipids (hereinafter, it may be referred to as the composition or the thermally coagulated product) can be obtained.

It is also possible that lipids are extracted from the solids containing lipids or a dried product thereof. With regard to a method for extraction of the lipids, although there is no particular limitation as long as it is a commonly used method, extraction with solvent, separation and removal of protein by means of pH adjustment, enzymatic treatment, etc., supercritical extraction, etc. or a combination thereof are used. Extraction with organic solvent, extracting with organic solvent after enzymatic treatment or supercritical extraction with carbon dioxide is preferably used. With regard to solvent used for the extraction with solvent, an appropriate organic solvent such as alcohol (e.g., methanol, ethanol, propanol, isopropanol, butanol, propylene glycol and butylene glycol), methyl acetate, ethyl acetate, acetone, chloroform, toluene, pentane, hexane, cyclohexane, etc. may be used solely or jointly by combining two or more thereof. Mixed liquid of hexane with ethanol is preferably used to extract the lipids. At that time, a mixing ratio of the solvents or a ratio of the material (the solid containing lipids) to the solvent may be freely set. With regard to the enzyme used for the enzymatic treatment, although there is no particular limitation as long as it is able to be used for foods, protease such as Alkalase (registered trade mark) (manufactured by Novozymes), protease A, M or P, pancreatin F (manufactured by Amano Enzyme), etc are used. The pH, the temperature condition, etc. for the enzymatic treatment can be set depending on the enzyme used and, for example, the method which is described in "Atarashii Shokuhin Kako Gijutsu I" edited by Takashi Yamashita (Kogyo Gijutsukai, 1986, pages 204 to 284) may be referred to. With regard to the supercritical extraction method using carbon dioxide, it may be carried out according to a common method and, for example, the method mentioned in "Atarashii Shokuhin Kako Gijutsu I" edited by Takashi Yamashita (Kogyo Gijutsukai, 1986, pages 79 to 102) may be referred to. In accordance with the above-mentioned methods, the lipids containing a lot of phospholipid are able to be manufactured from crustaceans easily and at a low cost.

In the solids containing lipids prepared by the method of the present invention, the lipids are concentrated in an efficient manner. The solids containing lipids contains 30% by weight or more, preferably contains 40% by weight or more of lipids in the total solid. The feature of the solid is that 50% or more by weight of the lipids as are phospholipids. The solids containing lipids or a dried product thereof or the lipids which are extracted therefrom by the above-mentioned method contain(s) the phospholipid abundantly. The lipids which further contain highly unsaturated fatty acids such as EPA and DHA is prepared which is able to be used as a material for pharmaceuticals, an ingredient for food or feed. A method for drying the solid may be in accordance with the common method.

The present invention also relates to a composition comprising proteins and lipids derived from squeezed liquid of crustaceans which is a composition comprising oils and fats and comprises 35% or more by weight or, preferably, comprises 40% or more by weight of lipids. Said composition is able to be prepared by the above-mentioned method. Additionally, 50% or more by weight of the lipids contained in this composition is phospholipid in which 15% or more by weight of EPA and DHA are contained. This composition contains the lipids which abundantly contain phospholipid and highly unsaturated fatty acids such as EPA and DHA. The lipids may be used as a material for pharmaceuticals, an ingredient for food or feed, etc.

For example, it is possible to carry out hot air drying or drying by means of steam. In addition, drying may be carried out by heating with high frequency waves or microwaves, vacuum/reduced pressure drying, freezing and thawing, or by means of a desiccant, and these methods may be used in combination. Because oxidized lipids cause unpleasant odors if the temperature is too high during the drying process, the drying should be carried out at 90° C. or lower, preferably 75° C. or lower, and more preferably 55° C. or lower. The drying may be carried out after preparing the solids containing lipids, and if washing with water is then carried out, drying may also be carried out after the washing. In cases where caught krill are used to prepare solids containing lipids at sea, the drying should be carried out prior to transport for reasons of transport costs. In view of the performance of the equipment and so on, if the drying is being carried out at sea, it is possible to stop part way through the drying process, land, and then restart the drying process on land. The reason for this is that as long as no unpleasant odors are generated due to the lipid-containing solids being exposed to high temperatures between the drying process carried out at sea and the drying process carried out on land, it is possible to eliminate krill odor and the source of the unpleasant odors by subsequent washing with water. In addition, because there are concerns regarding the krill putrefying in the case of long transport periods, it is preferable to refrigerate or freeze the krill before transportation.

In addition, solids containing lipids obtained using the method of the present invention contain large quantities of astaxanthin. In crustaceans, astaxanthin is largely contained in tissue, and because breakdown of tissue within crustaceans is insufficient if only heat treatment is carried out, it is possible to concentrate lipids that contain large quantities of astaxanthin by squeezing krill. With regard to a method for squeezing, there is no particular limitation as long as it is a commonly used one. For example, an oil hydraulic squeezing machine, a screw press, a meat separator, a press dehydrating machine, a centrifugal separator or a combination thereof can be used. Increasing the degree of squeezing increases the degree of breakdown of the tissue within the crustaceans and increases the astaxanthin concentration in the lipids, but if the degree of squeezing is excessive, problems relating to lipid concentration occur, as mentioned above. Therefore, in order to increase the quantity of astaxanthin contained in the lipids and therefore facilitate concentration of the lipids, it is preferable that the whole crustacean or a part thereof is squeezed to obtain a squeezed liquid corresponding to an amount of 5 to 50% of the wet weight. With methods in which the whole crustacean or a part thereof is not squeezed, it is not possible to obtain the astaxanthin contained in the tissue within the crustaceans, and such methods are therefore not suitable for achieving this type of objective. Of the lipids contained in solids containing lipids obtained in this way, it is possible for the astaxanthin content to be 100 ppm, and preferably 150 ppm.

In addition, the present invention also relates to a composition including proteins and lipids derived from a squeezed liquid of crustaceans which is a composition containing lipids that contains 30% or more by weight, and preferably 40% or more by weight, of lipids. Furthermore, the present invention also relates to a composition containing lipids characterized in that, in addition to these characteristics, 40% or less of the ash content is sodium chloride. Furthermore, the present invention also relates to a composition containing lipids characterized in that, in addition to these characteristics, the composition contains 100 ppm or more of astaxanthin. Said composition is able to be prepared by the above-mentioned method. Of the lipids contained in this composition, 50% by weight or more are phospholipids and 15% by weight or more are EPA and/or DHA. This composition contains the lipids which abundantly contain phospholipid and highly unsaturated fatty acids such as EPA and DHA. The lipids may be used as a material for pharmaceuticals, an ingredient for food or feed, etc.

Although Examples of the present invention will be described as follows, the present invention is not limited thereto.

Example 1

Preparation of Squeezed Liquid of Krill (by a Batch Method) and a Heating Treatment Antarctic krill of at least 45 mm length (400 kg) collected in the Antarctic Ocean in late July of 2005 followed by an immediate freezing at −30° C. was thawed by airing at room temperature (15° C.). The thawed krill was squeezed using an oil hydraulic squeezing machine (manufactured by Tokyo Techno; material cell=about 2 cm' about 68 cm' about 40 cm height) with a squeezing rate (yield of the squeezed liquid to the supplied amount of the thawed krill) of 13% by weight (lot 1) or 26% by weight (lot 2). The squeezed liquid was combined with the previously prepared thawed drips and heated in a steaming type heating kettle (kneader) having a capacity of 1 ton. The heating was stopped when the temperature reached to 95° C. and the resulting thermally coagulated product (a solid containing lipids) was classified using a commercially available sieve basket made of stainless steel by means of a natural dropping. The thermally coagulated product was dried using a vacuum drier of a steam heating type (Ribocone manufactured by Okawara Mfg.; type RM 200 VD) to give 9.0 kg (lot 1) or 15.9 kg (lot 2) of a dried product. Components in the raw material krill and in the resulting dried thermally coagulated products are shown in Table 1.

TABLE 1

| | | Raw | Dried Thermally Coagulated Product | |
|---|---|---|---|---|
| | | material | Lot 1 | Lot 2 |
| Squeezing Recovery | (wt %) | — | 13 | 26 |
| Water | (wt %) | 80.9 | 1.8 | 2.0 |
| Total Lipids | (dry wt %) | 17.4 | 51.2 | 51.8 |
| Crude Proteins | (dry wt %) | 67.7 | 40.1 | 40.1 |
| Ash | (dry wt %) | 15.6 | 8.7 | 8.1 |

As a result, it was confirmed that the lipids were efficiently concentrated from crustaceans by the method of the present invention. Then the lipids in the resulting thermally coagulated product (solids containing lipids) were analyzed. The resulting lipid composition and the representative fatty acid composition are shown in Table 2. With regard to the lipid composition, each lipid component separated by a developing solvent of benzene:chloroform:acetic acid (150:60:1.5) was quantified using a thin-layer automatic detecting device (manufactured by Mitsubishi Kagaku Iatron; type Iatroscan (registered trade mark) MK-6). With regard to the fatty acid composition, the constituting fatty acids were made into methyl esters in boron trifluoride and analyzed by a gas chromatography (Agilent Technologies; type 6890 N). The column for the gas chromatography used therefor was DB-WAX (Catalog No. 122-7032) of J & W Scientific. With regard to a carrier gas, helium was used and hydrogen flame ionization detector was used as a detector.

The dried product of the present thermally coagulated product did not show denaturation based on judgment by way of smell, color, etc. even when it is stored at room temperature for one year and the lipid component thereof was not oxidized but was retained stably. Further, as shown in Tables 1 and 2, the components of the thermally coagulated product of the present invention are useful as ingredients for livestock and marine feeds.

TABLE 2

| | | Lot 1 | Lot 2 |
|---|---|---|---|
| Lipid Composition | Triglycerides | 33 | 40 |
| | Free Fatty Acids | trace | trace |
| | Phospholipid | 67 | 59 |
| Fatty Acid Composition | C14:0 | 12.1 | 12.0 |
| | C16:0 | 20.1 | 20.0 |
| | C18:1 | 17.5 | 17.7 |
| | C18:2 | 2.0 | 1.9 |
| | C18:3 | 1.3 | 1.2 |
| | C18:4 | 3.3 | 3.2 |
| | EPA | 11.7 | 11.8 |
| | DHA | 5.5 | 5.6 |

Example 2

Preparation of Squeezed Liquid of Krill (by a Screw Press) and Heating Treatment The same krill as in Example 1 was thawed by airing at room temperature (8° C.) and the thawed drips were removed therefrom. The resulting thawed krill was placed in a screw press dehydrating machine (manufactured by Fukoku Kogyo; type SHZ-200' 1.5 ML) and treated with squeezing liquid rates (yields of the squeezed liquid to the supplied amount of the thawed krill) of 17 to 36% by weight to prepare squeezed liquids (lots 3 to 6). About 5 kg of each of the squeezed liquids was heated in a 50 L a steaming type heating kettle (rice boiler), heating was stopped when the temperature was confirmed to reach 95° C. The resulting thermally coagulated product (solids containing lipids) was classified using a commercially available sieve basket made of stainless steel by means of a natural dropping. Yield and components in the resulting thermally coagulated product of each lot are shown in Table 3. The yield is given in terms of the ratio by weight to the thawed raw material used. Moreover, dry weight (%) means the weight percentage of each component relative to the weight obtained by subtracting the weight of water from the overall weight (unless indicated otherwise, this is also the case in the following examples).

TABLE 3

|  |  | Thermally Coagulated Product | | | |
|---|---|---|---|---|---|
|  |  | Lot 3 | Lot 4 | Lot 5 | Lot 6 |
| Squeezing Recovery | (wt %) | 36 | 32 | 20 | 17 |
| Yield | (wt %) | 10.7 | 10.2 | 6.3 | 6.3 |
| Water | (wt %) | 65.5 | 69.1 | 65.7 | 66.1 |
| Total Lipids | (dry wt %) | 49.9 | 46.8 | 50.7 | 51.0 |
| Crude Proteins | (dry wt %) | 42.3 | 45.1 | 41.4 | 41.1 |
| Ash | (dry wt %) | 7.8 | 8.1 | 7.9 | 7.9 |

As a result, it was confirmed that the lipids were efficiently concentrated from crustaceans by the method of the present invention. Furthermore, the lipids in the resulting thermally coagulated product (solids containing lipids) were analyzed in the same manner as in Example 1. The results are shown in Table 4 and Table 5, respectively.

TABLE 4

|  |  | Lot 4 | Lot 5 |
|---|---|---|---|
| Lipid Composition | Triglycerides | 31 | 34 |
|  | Free Fatty Acids | 8 | 8 |
|  | Phospholipid | 59 | 57 |

TABLE 5

|  |  | Lot 3 | Lot 6 |
|---|---|---|---|
| Fatty Acid Composition | C14:0 | 11.4 | 11.5 |
|  | C16:0 | 20.1 | 20.0 |
|  | C18:1 | 17.7 | 17.8 |
|  | C18:2 | 1.9 | 1.8 |
|  | C18:3 | 1.2 | 1.2 |
|  | C18:4 | 2.9 | 2.9 |
|  | EPA | 13.1 | 13.2 |
|  | DHA | 6.8 | 6.7 |

Example 3

Preparation of Squeezed Liquid from Krill (by a Meat Separator) and Heating Treatment 10 tons of Antarctic krill of at least a 45 mm length collected in the Antarctic Ocean in mid-July of 2006 was squeezed using a meat separator (manufactured by Baader; type: BAADER 605) immediately after fishing to give 3 tons of squeezed liquid. It was immediately frozen. The frozen squeezed liquid was heated in a steaming type heating kettle and the heating was stopped when temperature reached 95° C. The whole heating product was placed into a centrifugal dehydrating machine (manufactured by Taieiseisakusho; type DT-1) using a filter cloth of 200 meshes and an extract (filtrate) was separated to give a thermally coagulated product (solids containing lipids). Components in the raw material and in the thermally coagulated product are shown in Table 6.

TABLE 6

|  |  | Raw material | Thermally Coagulated Product |
|---|---|---|---|
| Water | (wt %) | 81.6 | 60.4 |
| Total Lipids | (dry wt %) | 31.7 | 46.7 |

TABLE 6-continued

|  |  | Raw material | Thermally Coagulated Product |
|---|---|---|---|
| Crude Proteins | (dry wt %) | 56.0 | 47.0 |
| Ash | (dry wt %) | 12.3 | 6.3 |

As a result, it was confirmed that the lipids were efficiently concentrated from crustaceans by the method of the present invention. Furthermore, the lipids in the resulting thermally coagulated product (solids containing lipids) were analyzed in the same manner as in Example 1. The result is shown in Table 7.

TABLE 7

|  |  | Raw material | Thermally Coagulated Product |
|---|---|---|---|
| Lipid Composition | Triglycerides | 30 | 31 |
|  | Free Fatty Acids | 2 | trace |
|  | Phospholipid | 66 | 65 |
| Fatty Acid Composition | C14:0 | 11.8 | 12.0 |
|  | C16:0 | 22.4 | 22.8 |
|  | C18:1 | 19.8 | 20.0 |
|  | C18:2 | 1.7 | 1.6 |
|  | C18:3 | 1.0 | 1.0 |
|  | C18:4 | 1.7 | 1.7 |
|  | EPA | 13.6 | 13.1 |
|  | DHA | 6.6 | 6.0 |

Example 4

Extraction of Lipids from a Thermally Coagulated Heated Squeezed Liquid Using Chloroform Dried product (10 g) of the thermally coagulated product (solids containing lipids) prepared in Example 3 was homogenized in 100 mL of chloroform to give an extract oil 3.71 g. The extract oil was adsorbed with a column of silica gel (manufactured by Asahi Glass; Microsphere Gel; catalog number MS Gel Sil; 300 g) and then neutral lipids, etc. were washed with chloroform. After that, moving bed was changed to be methanol to recover 0.228 g of phospholipid. Analytical value of the lipids in 10 g of the dried thermally coagulated product was 4.72 g. The resulting phospholipid was tested with an Introscan analyser (the developing solvent comprises chloroform, methanol and water in 65:25:4). The phospholipid was found to be composed of 96% by weight of phosphatidylcholine and 4% by weight of phosphatidyl ethanolamine. Fatty acid composition of the phospholipid prepared in the Example was also analyzed by the same way as in Example 1. The result is shown in Table 8.

TABLE 8

| Fatty Acids | Total Lipids (Extract Oil) | Phospholipid |
|---|---|---|
| C14:0 | 12.0 | 2.3 |
| C16:0 | 22.8 | 26.1 |
| C18:1 | 20.0 | 10.4 |
| C18:2 | 1.6 | 2.1 |
| C18:3 | 1.0 | 1.4 |
| C18:4 | 1.7 | 1.6 |
| EPA | 13.1 | 29.7 |
| DHA | 6.1 | 12.1 |

As a result, it was confirmed that, when only phospholipid was taken out from the extract oil, purity of highly unsaturated fatty acids such as EPA and DHA became high.

Example 5

Extraction of Lipids from Coagulated Product of Heated Squeezed Liquid Using Hexane-Ethanol Lipids were extracted from 2.00 g of a dried product (analytical value of total lipid content was 0.94 g) of the thermally coagulated product (the solids containing lipids) prepared in Example 3 with 50 mL of a hexane-ethanol mixture (the solids containing lipids:solvent=1:25). The lipids were used for an extraction where the mixing ratio of the two kinds of solvents was varied from 100:0 to 0:100 to compare the extracting efficiency. Yield of the extract oil and purity of the phospholipid used in a lipid analysis by anIatroscan analyser are shown in Table 9.

TABLE 9

| Hexane (vol %) | 100 | 80 | 60 | 50 | 40 | 20 | 0 |
|---|---|---|---|---|---|---|---|
| Ethanol (vol %) | 0 | 20 | 40 | 50 | 60 | 80 | 100 |
| Extract Oil (g) | 0.79 | 0.89 | 0.97 | 0.97 | 0.94 | — | — |
| Extraction Yield (wt %) | 84 | 94 | 103 | 103 | 100 | — | — |
| Purity (%) | 55 | 65 | 66 | 65 | 64 | 67 | 65 |

As a result, when a mixing ratio of hexane was 20% or less in the test, water remained in the removal of the solvent from the extract oil by a vacuum concentration whereby an emulsion was formed and, therefore, no yield was determined. However, when the mixing ratio of hexane was from 40 to 80%, the lipids were able to be recovered in a yield of 90% or higher. On the other hand, it was confirmed that purity of the phospholipid in the extract oil was almost constant in any mixing ratio of the solvents other than the case where 100% of hexane was used.

Example 6

Investigation of Solvent Amount in Extraction with Solvent

Dried product of the thermally coagulated product (the solids containing lipids) prepared from the squeezed liquid of krill in Example 3 was used and the same procedure as in Example 6 was carried out using a solvent comprising hexane and ethanol in a mixing ratio of 60:40 to obtain extracted oil. However, ratio of the material, solid containing lipids, to the solvent was varied from 1:5 to 1:20. The analytical result for the extracted oil is shown in Table 10.

TABLE 10

| Ratio of Material:Solvent | 1:5 | 1:10 | 1:20 |
|---|---|---|---|
| Extraction Yield (wt %) | 75 | 86 | 94 |
| Purity of phospholipid (%) | 61 | 59 | 63 |

As a result, it was confirmed that purity of the phospholipid in the extract oil was almost constant even when the ratio of the solvents was varied.

Example 7

Separation of Extracted Oil in the Thermally Coagulated Product by a Treatment with Protease Distilled water (30 g) was added to 3 g of the thermally coagulated product (the solids containing lipids) prepared in Example 3 and a homogenizing treatment was carried out. The thermally coagulated product was uniformly dispersed. To the liquid (pH 7.5), 1 mL of a commercially available liquid enzyme (Alkalase 2.4 L; manufactured by Novozymes) or 1 mg of a commercially available powdery enzyme (Protease A, Protease M, Protease P or Pancreatin F manufactured by Amano Enzyme) and an enzymatic reaction was carried out at 50° C. for 2 hours. After that, pH of the reaction solution was adjusted to 1.4 using 2N hydrochloric acid and the solution was separated by centrifugation (2230 g for 10 minutes) at 50° C. The whole liquid layer containing the oil separated out in the surface layer was recovered. Each of the lipids contained in the whole liquid layer and in the precipitate was quantified by a mixed solvent comprising chloroform and methanol (2:1) and the recovering rate was determined. The result is shown in Table 11.

TABLE 11

| (wt %) | Liquid Layer | Precipitate | Total |
|---|---|---|---|
| No Enzyme | 24 | 82 | 106 |
| Alkalase | 40 | 67 | 107 |
| Protease A | 31 | 72 | 103 |
| Protease M | 27 | 72 | 99 |
| Protease P | 34 | 71 | 105 |
| Pancreatin F | 28 | 71 | 99 |

As a result, it was confirmed that liberation of the lipids from the thermally coagulated product (the solids containing lipids) to a liquid layer proceeded when an enzymatic treatment was carried out.

Example 8

Extraction of Lipids from the Thermally Coagulated Product by Supercritical Carbon Dioxide The thermally coagulated product (the solids containing lipids where the water content was 61.2% by weight) prepared in Example 3 or a dried product thereof (water content was 2.0% by weight) was used and an extraction of the lipid component using supercritical carbon dioxide was carried out under the condition of 34.3 MPa and 40° C. to give an extract and a residue after the extraction. The result is shown in Table 12.

TABLE 12

| | Materials for Extraction | |
|---|---|---|
| | Thermally Coagulated Product | Dried Thermally Coagulated Product |
| Amount of the Materials Used (g) | 103.7 | 101.9 |
| Extracted Amount (g) | 40.3 | 24.5 |
| Recovered Amount of Residue (g) | 79.2 | 77.4 |

Lipid composition was analyzed by the same manner as in Example 1 for the lipids in the resulting extract and in the residue after extraction. The result is shown in Table 13. In the table, TG, FFA and PL mean triglycerides, free fatty acids and phospholipid, respectively.

TABLE 13

| | | Materials for Extraction | |
|---|---|---|---|
| | | Thermally Coagulated Product | Dried Thermally Coagulated Product |
| Extract | Triglycerides | 90 | 92 |
| | Free Fatty Acids | 3 | 1 |
| | Phospholipid | 1 | 0 |
| Residue after Extraction | Triglycerides | 0 | 1 |
| | Free Fatty Acids | 0 | 1 |
| | Phospholipid | 99 | 97 |

As a result, it was confirmed that triglycerides were predominately extracted in the extracting method regardless of the dried state of the thermally coagulated product (the solids containing lipids) and that, in the residue after the extraction, phospholipid was predominately concentrated.

Example 9

Fish Body Size of Antarctic Krill and Heating Treatment of Squeezed Liquid

Antarctic krill with a length of 30 mm to 44 mm (20 kg) which was fished in the Antarctic Ocean during April to August of 2007 followed by an immediate freezing at −30° C. was thawed with airing for one night in a freezer (4° C.). The thawed krill were squeezed at the squeezing rate (yield of the squeezed liquid to the supplied amount of the thawed krill) of 40 to 45% by weight using a filter screw press (manufactured by Arai Machinery; type MM-2). About 5 kg of the resulting squeezed liquid was heated in a 50-L steaming type heating kettle of (rice boiler) and, when the temperature was confirmed to reach 95° C., the heating was stopped. The resulting thermally coagulated product (the solids containing lipids) was classified by a natural dropping method using a commercially available sieve basket made of stainless steel. The same experiment was performed times using different lots of krill components of the raw material and of the resulting thermally coagulated product are shown in Table 14 and Table 15, respectively. Additionally, lipid composition and fatty acid composition of the thermally coagulated product are shown in Table 16.

TABLE 14

| | Raw materials | | | |
|---|---|---|---|---|
| | | Lot 7 | Lot 8 | Lot 9 |
| Water | (wt %) | 81.8 | 83.5 | 82.1 |
| Total Lipids | (dry wt %) | 15.9 | 12.1 | 15.6 |
| Crude Proteins | (dry wt %) | 67.0 | 69.7 | 67.6 |
| Ash | (dry wt %) | 15.9 | 17.6 | 16.2 |
| Crude Fiber | (dry wt %) | 2.2 | 2.4 | 2.8 |

TABLE 15

| | Thermally Coagulated Product | | | |
|---|---|---|---|---|
| | | Lot 7 | Lot 8 | Lot 9 |
| Water | (wt %) | 78.9 | 79.2 | 76.5 |
| Total Lipids | (dry wt %) | 37.9 | 30.8 | 33.2 |
| Crude Proteins | (dry wt %) | 59.2 | 65.9 | 63.8 |
| Ash | (dry wt %) | 10.9 | 12.5 | 11.1 |

TABLE 16

| Material Lot | | Lot 7 | Lot 8 | Lot 9 |
|---|---|---|---|---|
| Lipid Composition | Triglycerides | 39.9 | 29.4 | 33.5 |
| | Free Fatty Acids | 8.7 | 8.5 | 8.4 |
| | Phospholipid | 49.0 | 59.7 | 54.7 |
| Fatty Acid Composition | C14:0 | 10.4 | 9.5 | 10.8 |
| | C16:0 | 19.0 | 20.9 | 21.5 |
| | C18:1 | 15.6 | 18.7 | 19.2 |
| | C18:2 | 2.1 | 1.8 | 1.8 |
| | C18:3 | 1.8 | 1.2 | 1.0 |
| | C18:4 | 4.4 | 2.1 | 1.9 |
| | EPA | 15.2 | 15.0 | 14.1 |
| | DHA | 8.4 | 8.8 | 7.6 |

Example 10

Mass Production of Thermally Coagulated Product of Squeezed Krill Liquid 10 tons of Antarctic krill at least 45 mm in length collected in the Antarctic Ocean in mid-June of 2008 were squeezed using a meat separator (manufactured by Baader; type: BAADER 605) immediately after being caught to give 3 tons of squeezed liquid. 800 kg of this squeezed liquid was placed in a stainless steel tank and heated by directly introducing steam at 140° C. After heating for approximately 60 minutes, it was confirmed that the temperature had reached 85° C., and the heating was then stopped. A valve in the bottom of the tank was opened, the liquid component was removed by being allowed to pass through a mesh having an aperture size of 2 mm by means of gravity, the solid component (thermally coagulated product) was washed by being showered with an equal quantity of water, and 12 kg batches of the thermally coagulated product were placed in aluminum trays and rapidly frozen using a contact freezer. Components in the resulting thermally coagulated products are shown in Tables 17 and 18. In addition, similar experiments were carried out eight times using a total of eight lots produced between May and August 2008, and the average values and standard deviations of these lots are shown in Tables 17 and 18. Moreover, in these tables, TG denotes triglycerides, FFA denotes free fatty acids, and PL denotes phospholipids.

TABLE 17

| | | Mid-June | May to August average ± SD* |
|---|---|---|---|
| Water | (%) | 76.9 | 77.8 ± 2.0 |
| Total Lipids | (dry wt %) | 47.6 | 43.7 ± 6.7 |
| Crude Proteins | (dry wt %) | 40.3 | 39.8 ± 5.7 |
| Ash | (dry wt %) | 11.3 | 12.4 ± 1.3 |

*SD = Standard Deviations

TABLE 18

| | | Mid-June | May to August average ± SD* |
|---|---|---|---|
| Lipid Composition (%) | TG | 41.3 | 41.4 ± 1.7 |
| | FFA | 1.7 | 1.7 ± 0.4 |
| | PL | 52.7 | 54.1 ± 1.3 |
| Fatty Acid Composition (%) | C14:0 | 11.8 | 11.4 ± 0.5 |
| | C16:0 | 21.7 | 21.0 ± 0.8 |
| | C18:1 | 18.8 | 18.2 ± 1.0 |
| | C18:2 | 1.4 | 1.5 ± 0.2 |
| | C18:3 | 1.1 | 1.2 ± 0.2 |
| | C18:4 | 2.3 | 2.6 ± 0.7 |

TABLE 18-continued

|  | Mid-June | May to August average ± SD* |
|---|---|---|
| EPA | 13.8 | 14.2 ± 0.7 |
| DHA | 6.2 | 6.7 ± 0.8 |

Example 11

Washing and Drying of Thermally Coagulated Product 1 ton of thermally coagulated product produced in example 10 and then stored for 3 months in a freezer was placed in 3000 liters of water, heated under stirring and then held for 10 minutes at a temperature of 65° C. The water was removed via 24 mesh nylon, and the solid component was placed in 3000 liters of water (at 20° C.). After stirring for 15 minutes, the water was removed via 24 mesh nylon, and 564 kg of solid component (water content 73%) was obtained by treating for 15 seconds in a centrifugal dehydrating machine (manufactured by Tanabe; type O-30). 1.54 kg of tocopherol was added to this solid component, blended in a mixer, and then dried for 3.2 hours at a hot air temperature of 60° C. so as to obtain 148.4 kg of washed and dried product. Components in the resulting washed and dried product are shown in Tables 19 and 20.

TABLE 19

|  |  | Washed and Dried Product |
|---|---|---|
| Water | (%) | 2.1 |
| Total Lipids | (dry %) | 49.6 |
| Crude Proteins | (dry %) | 46.4 |
| Ash | (dry %) | 4.3 |

TABLE 20

|  |  | Washed and Dried Product |
|---|---|---|
| Fatty Acid Composition (%) | C14:0 | 10.7 |
|  | C16:0 | 20.1 |
|  | C18:1 | 17.9 |
|  | C18:2 | 1.9 |
|  | C18:3 | 1.2 |
|  | C18:4 | 2.5 |
|  | EPA | 14.0 |
|  | DHA | 6.8 |

Example 12

Extraction of Lipids from Washed and Dried Product of Thermally Coagulated Product 1200 liters of 99% ethanol was added to 299.6 kg of the washed and dried product produced in example 11, heated to 60° C., and stirred for 2 hours. Solid-liquid separation was then carried out by means of gravity, using 100 mesh nylon, so as to obtain an extraction liquid (A) and an extraction meal (a). 800 liters of 99% ethanol was added to the extraction meal (a), heated to 60° C. and stirred for 2 hours, after which solid-liquid separation was then carried out using 100 mesh nylon so as to obtain an extraction liquid (B) and an extraction meal (b). 700 liters of 99% ethanol was added to the extraction meal (b), heated to 60° C., and stirred for 2 hours, after which solid-liquid separation was then carried out using 100 mesh nylon so as to obtain an extraction liquid (C) and 390 kg of an extraction meal (c) (the reduction in weight after drying at 105° C. for 4 hours was 61.8%). When the extraction liquid (A), extraction liquid (B), and extraction liquid (C) were combined, the total weight thereof was 2089 kg. These combined extraction liquids were concentrated under reduced pressure at a temperature of 60° C. or lower, and the ethanol and water were removed so as to obtain 141.6 kg of extracted lipids. Components in the resulting extracted lipids are shown in Tables 21 and 22.

TABLE 21

|  |  | Extracted Lipids |
|---|---|---|
| Water | (%) | 0.41 |
| Ethanol | (%) | 0.21 |
| Sodium | (%) | 0.10 |
| Phospholipid | (%) | 44.8 |
| Acid Number |  | 4.22 |
| Peroxide Value | (meq/kg) | <0.1 |
| Astaxanthin | (ppm) | 337 |

TABLE 22

|  |  | Extracted Lipids |
|---|---|---|
| Fatty Acid Composition (%) | C14:0 | 8.2 |
|  | C16:0 | 19.4 |
|  | C18:1 | 15.1 |
|  | C18:2 | 1.9 |
|  | C18:3 | 1.4 |
|  | C18:4 | 2.3 |
|  | EPA | 18.8 |
|  | DHA | 11.7 |

Example 13

Comparison of Lipid Weights in Thermally Coagulated Products of Squeezed Krill Liquids (Live) krill collected in the Antarctic Ocean between June and July 2008 and then frozen were allowed to thaw to room temperature. This krill was squeezed using 30 mesh nylon at a squeezing ratio required to obtain squeezed liquids corresponding to an amount of 5 to 50 of the total weight. Each obtained squeezed liquid was heated at 85° C. or higher for 5 minutes so as to produce thermally coagulated products. In addition, the thermally coagulated product obtained from a squeezed liquid having a squeezing ratio of 50% was washed twice with a quantity of water corresponding to twice the quantity of the thermally coagulated product, and the resulting washed product was dried for 4 hours while being agitated with hot air at 60° C. so as to obtain a washed and dried product of the thermally coagulated product. The analysis values for each thermally coagulated product are shown in Table 23. The lipids, proteins, and ash content in the table are expressed in terms of wt. % relative to the total weight, and the water content was calculated by subtracting these contents from 100% in the case of A to D and by actual measurement in the case of E. The composition of each lipid is expressed in terms of wt. % of each component relative to the overall lipid content. The total lipid content is expressed in terms of wt. % of the lipid relative to the total solid content, that is, to the total weight of lipids, proteins, and ash.

TABLE 23

|  |  | A | B | C | D | E |
|---|---|---|---|---|---|---|
| Water | (%) | 77.8 | 77.5 | 81.3 | 81.7 | 2.4 |
| Lipids | (%) | 8.7 | 7.8 | 6.7 | 6.3 | 46.0 |
| Crude Proteins | (%) | 11.3 | 12.4 | 9.8 | 9.8 | 44.9 |
| Ash | (%) | 2.2 | 2.3 | 2.2 | 2.2 | 4.2 |
| Fatty Acid | C14:0 | 10.8 | 1.0 | 11.2 | 11.0 | 11.1 |
| Composi- | C16:0 | 20.0 | 20.4 | 20.1 | 19.9 | 20.2 |
| tion (%) | C18:1 | 18.7 | 18.9 | 18.6 | 18.6 | 18.3 |
|  | C18:2 | 1.4 | 1.4 | 1.4 | 1.4 | 1.9 |
|  | C18:3 | 1.1 | 1.1 | 1.1 | 1.1 | 1.3 |
|  | C18:4 | 2.2 | 2.1 | 2.3 | 2.3 | 2.6 |
|  | EPA | 13.9 | 14.2 | 13.8 | 13.7 | 13.7 |
|  | DHA | 6.6 | 6.8 | 6.2 | 6.2 | 6.7 |
| Total Lipids | (%) | 39.2% | 34.7% | 35.8% | 34.4% | 48.4% |

*A: Squeezing ratio 50% coagulated product
*B: Squeezing ratio 30% coagulated product
*C: Squeezing ratio 12% coagulated product
*D: Squeezing ratio 5% coagulated product
*E: Squeezing ratio 50% washed and dried product of the coagulated product In the "Okean" (dried paste) disclosed in non-patent document 5, it is understood that the lipid content is 23.0 to 28.4%, while the total lipid content in the squeezed thermally coagulated product (dried product) is 34.4 to 39.2%, from which it is understood that the lipid content in the squeezed thermally coagulated product is extremely high.

In addition, because water-soluble proteins and ash are washed away by washing with water, it is understood that the weight percentage of lipids per solid content is higher after washing with water than before.

INDUSTRIAL APPLICABILITY

The present invention is useful as a method for producing of lipids which abundantly contain phospholipid easily and at a low cost. The solid which comprises the lipids prepared by said method or a dried product thereof, the lipids extracted therefrom and a composition abundantly containing useful lipids derived from crustacean are useful as materials for pharmaceuticals, ingredients for foods and feed, etc. cm The invention claimed is:

The invention claimed is:

1. A method for concentrating lipids contained in a crustacean, comprising:
   heating a squeezed liquid at a temperature of not lower than 50° C., the squeezed liquid being prepared by squeezing the whole crustacean or a part thereof in an unheated state so as to break down tissue of the whole crustacean or a part thereof and to obtain the squeezed liquid; and
   separating the heated squeezed liquid into solids containing lipid components and liquid containing water-soluble components,
   wherein the solids containing lipid components and liquid containing water-soluble components are separated by filtration and/or centrifugal separation.

2. The method for concentrating the lipids according to claim 1, wherein the squeezed liquid is heated at the temperature where proteins contained in the squeezed liquid is coagulated.

3. The method for concentrating the lipids according to claim 1, wherein the crustacean is a crustacean which belongs to the order of Euphausiaceae.

4. A method for producing lipids, which comprises preparing the lipids from the solids containing the lipid components or a dried product thereof prepared by the method described in claim 1.

5. The method for producing the lipids according to claim 4, wherein the method for preparing the lipids is carried out by any one of an extraction with an organic solvent, an extraction with an organic solvent after carrying out an enzymatic treatment and a supercritical extraction.

6. The method of claim 1, wherein the squeezed liquid is heated at a temperature of less than or equal to 150° C.

7. The method of claim 1, wherein the whole crustacean or a part thereof is squeezed using at least one selected from the group consisting of an oil hydraulic squeezing machine, a screw press, a meat separator, a press dehydrating machine and a centrifugal separator.

8. Solids containing lipid components or a dried product thereof,
   wherein 50% or more by weight of the lipid components is phospholipid, and
   wherein the solids containing lipid components are prepared by
   heating a squeezed liquid at a temperature of not lower than 50° C., the squeezed liquid being prepared by squeezing a whole crustacean or a part thereof in an unheated state so as to break down tissue of the whole crustacean or a part thereof and to obtain the squeezed liquid, and
   separating the heated squeezed liquid into solids containing lipid components and liquid containing water-soluble components,
   wherein the solids containing lipid components and liquid containing water-soluble components are separated by filtration and/or centrifugal separation.

9. A method for producing phospholipid, which comprises carrying out a supercritical extraction of the solids containing the lipid components prepared by the method described in claim 1 or a dried product thereof to separate a triglyceride and preparing phospholipid from the residue after the extraction.

10. Solids obtained by washing solids containing lipid components or a dried product thereof with water, or a dried product thereof,
    wherein 50% or more of the lipid components are phospholipids, and
    wherein the solids containing lipid components are obtained by
    heating a squeezed liquid at a temperature of not lower than 50° C., the squeezed liquid being prepared by squeezing a whole crustacean or a part thereof in an unheated state so as to break down tissue of the whole crustacean or a part thereof and to obtain the squeezed liquid, and
    separating the heated squeezed liquid into solids containing lipid components and liquid containing water-soluble components,
    wherein the solids containing lipid components and liquid containing water-soluble components are separated by filtration and/or centrifugal separation.

* * * * *